United States Patent [19]

Van Tuttle et al.

[11] Patent Number: 5,175,274

[45] Date of Patent: Dec. 29, 1992

[54] THERAPEUTIC NUCLEOSIDES

[75] Inventors: Joel Van Tuttle, Durham; Thomas A. Krenitsky, Chapel Hill, both of N.C.

[73] Assignee: Burroughs Wellcome Co., Research Triangle Park, N.C.

[21] Appl. No.: 771,619

[22] Filed: Oct. 4, 1991

Related U.S. Application Data

[63] Continuation of Ser. No. 175,958, Mar. 31, 1988, abandoned.

[30] Foreign Application Priority Data

Apr. 3, 1987 [GB] United Kingdom ................ 8708050

[51] Int. Cl.$^5$ ............................................. C07H 17/00
[52] U.S. Cl. ..................................................... 536/24
[58] Field of Search ..................................... 536/24, 26

[56] References Cited

U.S. PATENT DOCUMENTS 4,751,221  6/1988  Watanabe et al. ................... 514/46

Primary Examiner—John W. Rollins
Attorney, Agent, or Firm—Donald Brown; Lawrence A. Nielsen; Hannah O. Green

[57] ABSTRACT

This invention relates to certain 2'-fluoro nucleosides and pharmaceutically acceptable derivatives thereof and their use in the treatment of HIV infections. Also provided are pharmaceutical formulations and processes for the production of the compounds according to the invention.

1 Claim, No Drawings

THERAPEUTIC NUCLEOSIDES

This is a continuation of copending application Ser. No. 07/175,958 filed on Mar. 31, 1988, now abandoned.

The present invention relates to certain 2'-fluoronucleosides for use in medical therapy particularly in the treatment of viral infections especially human retroviral infections.

AIDS is an immunosuppressive or immunodestructive disease that predisposes subjects to fatal opportunistic infections. Characteristically, AIDS is associated with a progressive depletion of T-cells, especially the helper-inducer subset bearing the OKT[4] surface marker.

Human Immunodeficiency Virus (HIV) has been reproducibly isolated from patients with AIDS or with signs and symptoms that frequently precede AIDS HIV is cytopathic and appears to preferentially infect and destroy OKT[4]-bearing T-cells, and it is now generally recognized that HIV is the etiological agent of AIDS.

Since the discovery of HIV as the etiological agent of AIDS, numerous proposals have been made for anti-HIV chemotherapeutic agents that may be effective in the treatment of AIDS. Thus, for example, European Patent Specification No. 196185 describes 3'-azido-3'-deoxythymidine (which has the approved name zidovudine) and its pharmaceutically acceptable derivatives and their use in the treatment of human retrovirus infections including AIDS and associated clinical conditions.

It has now been found that certain 2'-fluoronucleosides of general formula (I) below have exceptionally potent activity against HIV which renders the compounds and their derivatives useful in the treatment of AIDS and related conditions.

The above mentioned 2'-fluoronucleosides have the general formula

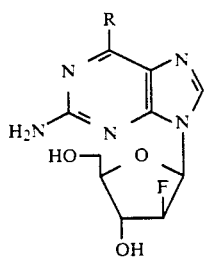

(I)

in which R represents hydrogen, hydroxy, $C_{1-6}$ alkyl, $C_{1-6}$ alkoxy (e.g. methoxy or ethoxy), amino or amino substituted by $C_{1-6}$ alkyl, $C_{1-6}$ alkoxy or $C_{3-6}$ cycloalkyl (e.g. cyclopropylamino). The compounds of formula (I) and their pharmaceutically acceptable derivatives are hereinafter referred to as the compounds according to the invention.

The compounds of formula (I) in which R is hydroxy or amino have previously been described in the literature; for example in J. A. Montgomery et al., J. Med. Chem., 1986, 29, 2389–92, which discloses the cytotoxic evaluation of the above compounds. The compound of formula (I) in which R is hydrogen is disclosed in European Patent Application 219,829.

The present invention further includes as new compounds the compounds of formula (I) above and their pharmaceutically acceptable derivatives with the exception of the compounds of formula (I) in which R is hydroxy, amino or hydrogen.

Particularly preferred compounds of the invention include:
1) 2,6-Diamino-9-(2-deoxy-2-fluoro-β-D-arabinofuranosyl)-9H-purine.
2) 9-(2-Deoxy-2-fluoro-β-D-arabinofuranosyl)guanine.
3) 2-Amino-6-(cyclopropylamino)-9-(2-deoxy-2-fluoro-β-D-arabinofuranosyl)-9H-purine.
4) 2-Amino-9-(2-deoxy-2-fluoro-β-D-arabinofuranosyl)-6-methoxy-9H-purine.
5) 2-Amino-9-(2-deoxy-2-fluoro-β-D-arabinofuranosyl)-6-ethoxy-9H-purine.
6) 2-Amino-9-(2-deoxy-2-fluoro-β-D-arabinofuranosyl)-9H-purine.

Compound 2 above is especially preferred on the basis of the high anti-HIV activity. Thus, in one aspect, the present invention provides a compound according to the invention for use in medical therapy particularly in the treatment of viral infections especially human retroviral infections.

Examples of retroviral infections which may be treated in accordance with the invention include human retroviral infections such as Human Immunodeficiency Virus (HIV), HIV-2 and Human T-cell Lymphotropic Virus (HLTV) e.g. HTLV-I or HTLV-IV infections. The compounds according to the invention are especially useful for the treatment of AIDS and related clincial conditions such as AIDS-related complex (ARC), progressive generalised lymphadenopathy (PGL), AIDS-related neurological conditions, such as multiple sclerosis or tropical paraparesis, anti-HIV antibody-positive and HIV-positive conditions, Kaposi's sarcoma and thrombocytopenic purpura. The compounds may also be used in the treatment of psoriasis.

In a further aspect, the present invention provides the use of a compound according to the invention in the manufacture of a medicament for the treatment of viral infections especially human retroviral infections.

The present invention further provides a method for the treatment of human retroviral infections which comprises administering to a human subject an effective amount of a compound according to the invention.

By "a pharmaceutically acceptable derivative" is meant any pharmaceutically acceptable salt, ester or salt of such ester, or any other compound which upon administration to the recipient is capable of providing (directly or indirectly) the parent compound of formula (I).

Preferred esters of the compounds of formula (I) include carboxylic acid esters in which the non-carbonyl moiety of the ester grouping is selected from straight or branched chain alkyl, alkoxyalkyl (e.g. methoxymethyl), aralkyl (e.g. benzyl) aryloxyalkyl (e.g. phenoxymethyl), aryl (e.g. phenyl) optionally substituted by halogen, $C_{1-4}$ alkyl or $C_{1-4}$ alkoxy); sulphonate esters such as alkyl- or aralkylsulphonyl (e.g. methansulphonyl); amino acid esters (e.g. L-valyl or L-isoleucyl); and mono-, di- or triphosphate esters.

With regard to the above-described esters, unless otherwise specified, any alkyl moiety present advantageously contains 1 to 18 carbon atoms, particularly 1 to 6 carbon atoms. Any aryl moiety present in such esters advantageously comprises a phenyl group.

Any reference to any of the above compounds also includes a reference to a pharmaceutically acceptable salt thereof.

Examples of pharmaceutically acceptable salts of the compounds of formula (I) include base salts such as alkali metals (e.g. sodium), alkaline earth metals (e.g.

magnesium), ammonium and $NX_4^+$ (wherein X is $C_{1-4}$ alkyl) salts.

The compounds according to the invention may be employed in medical therapy in combination with other therapeutic agents, for example 3'-azido-3'-deoxy thymidine (zidovudine), acyclic nucleoside derivatives such as 9-(2-hydroxyethoxymethyl)-guanine (acyclovir), 2',3'-dideoxynucleosides such as 2',3'-dideoxycytidine, 2',3'-dideoxyadenosine and 2',3'-dideoxyinosine, interferons such as alpha-interferon, nucleoside transport inhibitors such as dipyridamole, glucuronidation inhibitors such as probenicid, immunomodulators such as granulocyte macrophage colony stimulating factor (GMCSF) and other agents for example as described in European Patent Specification 217580. The component compounds of such combination therapy may be administered simultaneously, in either separate or combined formulations, or at different times e.g. sequentially such that a combined effect is achieved.

The compounds according to the invention, also referred to herein as the active ingredient, may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the infection and the chosen active ingredient.

In general a suitable dose will be in the range of 3.0 to 120 mg per kilogram body weight of the recipient per day, preferably in the range of 6 to 90 mg per kilogram body weight per day and most preferably in the range 15 to 60 mg per kilogram body weight per day. The desired dose is preferably presented as two, three, four, five, six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

Experiments suggest that a dose should be administered to achieve peak plasma concentrations of the active compound of from about 1 to about 75 $\mu M$, preferably about 2 to 50 $\mu M$, most preferably about 3 to about 30 $\mu M$. This may be achieved, for example, by the intravenous injection of a 0.1 to 5% solution of the active ingredient, optionally in saline, or orally administered as a bolus containing about 1 to about 100 mg/kg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible for the active ingredient to be administered alone, it is preferable to present it as a pharmaceutical formulation. The formulations of the present invention comprise at least one active ingredient, as above defined, together with one or more acceptable carriers thereof and optionally other therapeutic agents. Each carrier must be "acceptable" in the sense of being compatible with the other ingredients of the formulation and not injurious to the patient. Formulations include those suitable for oral, rectal, nasal, topical (including buccal and sublingual), vaginal or parenteral (including subcutaneous, intramuscular, intravenous and intradermal) administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulation are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach. This is particularly advantageous where the base is a purine, as such compounds are susceptible to acid hydrolysis.

Formulations suitable for topical administration in the mouth include lozenges comprising the active ingredient in a flavoured basis, usually sucrose and acacia or tragacanth; pastilles comprising the active ingredients in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredients such carriers as are known in the art to be appropriate.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may be include suspending agents and thickening agents. The formulations may be presented in unit-dose or multi-dose sealed containers, for example, ampoules and vials, and may be stored in a freeze-dried (lyophilized) condition requiring only the additions of the sterile carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of an active ingredient.

The present invention further includes a process for the preparation of a compound according to the invention and pharmaceutically acceptable derivatives thereof which comprises either:

(A) reacting a compound of formula:

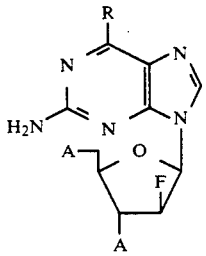

(wherein R is as herinbefore defined and A represents a precursor group for the hydroxy group, or for a pharmaceutically acceptable derivative group thereof) with an agent or under conditions serving to convert the said precursor group into the corresponding desired group; or (B) reacting a purine base of formula

B—H    (III)

wherein B is the required purine moiety of a compound according to the invention).
or a functional equivalent thereof, with a compound serving to introduce the desired arabinofuranosyl ring at the 9-position of the purine base of formula (III); or (C) for the preparation of a compound of formula (I) in which R is hydroxy, reacting the corresponding compound of formula (I) in which R is amino with an agent (e.g. adenosine deaminase) serving to convert the said amino group to a hydroxy group;

and thereafter, or simultaneously therewith, effecting one or more of the following optional conversions:

(i) when a compound of formula (I) is formed, converting it into a pharmaceutically acceptable derivative thereof, (ii) when a pharmaceutically acceptable derivative of a compound of formula (I) is formed, converting the said derivative into a compound of formula (I), or a different derivative thereof.

In the above-described process according to the invention, it will be appreciated that the precursor compounds of formula (I) as well as the above-mentioned agents and conditions, will be selected from those that are known in the art of nucleoside synthetic chemistry. Examples of such conversion procedures are described hereinafter for guidance and it will be understood that they can be modified in conventional manner depending on the desired compound of formula (I). In particular, where a conversion is described which would otherwise result in the undesired reaction of labile groups then such groups may be protected in conventional manner, with subsequent removal of the protecting groups after completion of the conversion.

With regard to process (A), A may represent a protected hydroxy group e.g. an ester grouping of the type referred to above in relation to formula (I) particularly acetoxy, or an ether group such as a trialkylsilyloxy group, e.g. t-butyldimethylsilyloxy or an aralkoxy group e.g. triphenylmethoxy. Such groups may be converted for example by hydrolysis to the desired hydroxy group or, by transesterification, to an alternative ester group.

With regard to process (B), this may be effected for example by treating an appropriate purine base of formula (III) or a salt or protected derivative thereof, with a 2'-deoxy-2'-fluoroarabinose derivative for example in the presence of the appropriate pentosyl transferring enzyme.

A compound of formula (I) may be converted into a pharmaceutically acceptable phosphate or other ester by reaction with respectively a phosphorylating agent, e.g. $POCl_3$ or an appropriate esterifying agent, e.g. an acid halide or anhydride. The compound of formula (I), including esters thereof, may be converted into pharmaceutically acceptable salts thereof in conventional manner, e.g. by treatment with an appropriate base. An ester or salt of a compound of formula (I) may be converted into the parent compound, e.g. by hydrolysis.

The following Examples are intended for illustration only and are not intended to limit the scope of the invention in any way. The term 'active ingredient' as used in the Examples means a compound of formula (I) or a pharmaceutically acceptable derivative thereof.

EXAMPLE 1

2,6-Diamino-9-(2-deoxy-2-fluoro-β-D-arabinofuranosyl)-9H-purine 2,6-Diaminopurine (Pacific Chemical Laboratories, 1.0 g, 6.4 mmoles) and 1-(2-Deoxy-2-fluoro-β-D-arabinofuranosyl)thymine (C. H. Tann et al., *J. Org. Chem.* 50:3647, 1985; 0.3 g, 1.2 mmoles) was suspended in 100 ml of 5 mM potassium phsophate buffer, pH 7.0, which contained 0.04% (w/v) potassium azide. Thymidine phosphorylase (160,000 I.U.) and purine nucleoside phosphorylase (290,000 I.U.) (T. A. Krenitsky et al., *Biochemistry,* 20:3615, 1981 and U.S. Pat. No. 4,381,444) absorbed onto 69 ml of DEAE-cellulose were added and the suspension shaken at 37° C. for 1 day. The suspension was then shaken at 50° C. for 1 day at which time 2.0 g of 2,6-diaminopurine was added. After shaking for 4 additional days at 50° C., the reaction was filtered. The filter cake was washed with water and the filtrates combined and the solvent removed under vacuum. The residue was dissolved in water and applied to a 2.5×17 cm AG1X2-hydroxide (Bio-Rad) column. After washing the column with water, the product was eluted with methanol/water (9/1). The product was further purified by chromatography on silica gel with acetonitrile/water (9/1) as the solvent followed by chromatography on silica gel with chloroform/methanol/water (80/20/2) as the solvent. After the solvent was removed under vacuum, the residue was dissolved in water and lyophilization yielded 0.2 g of title compound that analysed as a 1.4 hydrate.

Anal. Calcd. for $C_{10}H_{13}FN_6O_3 \cdot 1.4H_2O$.

Calcd.: C, 38.81; H, 5.15; N, 27.16; F, 6.14. Found: C, 38.66; H, 5.07; N, 26.83; F, 6.52.

Structure further confirmed by $^1$H-NMR.

EXAMPLE 2

9-(2-Deoxy-2-fluoro-β-D-arabinofuranosyl)guanine 2,6-Diamino-9-(2-deoxy-2-fluoro-β-D-arabinofuranosyl)-9H-purine (0.1 g, 0.35 mmoles) prepared as in Example 1, was dissolved in 10 ml of water.

Calf intestine adenosine deaminase (10 I.U., Boehringer Mannheim) was added and the solution incubated at 37° C. for one day. The solvent was removed under vacuum. The residue was dissolved in acetonitrile/water (85/15) and chromatographed on silica gel with acetonitrile/water (85/15) as the solvent. Product containing fractions were combined and the solvent removed under vacuum. The residue was dissolved in water and lyophilization yielded 0.14 g of the title compound that analysed as a 1.1 hydrate.

Anal. Calcd. for $C_{10}H_{12}FN_5O_4.1.1H_2O$.

Calcd.: C, 39.37; H, 4.69; N, 29.96; F, 6.23. Found: C, 39.46; H, 4.63; N, 22.98; F, 6.20.

Structure further confirmed by $^1$H-NMR.

EXAMPLE 3

2-Amino-6-(cyclopropylamino)-9-(2-deoxy-2-fluoro-β-D-arabinofuranosyl)-9H-purine a) 2-Amino-6-(cyclopropylamino)-9H-purine hydrochloride A solution of 2-amino-6-chloropurine (4.6 g, 27.5 mmole) and cyclopropylamine (12.5 g, 220 mmole 8 equiv) in MeOH (100 ml) was heated at 50° C. for 18 hours. Then 2-methoxyethanol (50 ml) was added, and the reaction was heated at 70° C. for an additional 6 hours. After cooling, a small amount of unreacted starting material was filtered off, and the filtrate was evaporated and purified on a silica gel column eluting with $CHCl_3$: 5% to 10% MeOH. The product was then recrystallised twice from MeOH and once from EtOH as a hydrochloride salt to give 1.45 g, (23%) of product; m.p. 253°–257° C., Anal. Calcd. for $C_8H_{10}N_6.HCl.1.25H_2O$.

Calcd.: C, 41.57; H, 5.01; N, 36.35; Cl, 15.34. Found: C, 41.55; H, 5.01; N, 36.28; Cl, 15.0.

b) 2-Amino-6-(cyclopropylamino)-9-(2-deoxy-2-fluoro-β-D-arabinofuranosyl)-9-H-purine 1-2-deoxy-2-fluoro-β-D-2-Amino-6-(cyclopropylamino)purine hydrochloride (0.5 g, 2.2 mmoles) and 1-(2-deoxy-2-fluoro-β-D-arabinofuranosyl)thymine (C. H. Tann et al., J. Org. Chem. 50:3647, 1985; 0.5 g; 1.9 mmoles) were dissolved in 6 ml of 5 mM potassium phosphate buffer, pH 7.0 which contained 0.04% (w/v) potassium azide. The pH of the solution was adjusted to 6.8 with potassium hydroxide. Thymidine phosphorylase (16,000 I.U) and purine nucleoside phosphorylase (5,500 I.U) (T. A. Krenitsky et al., *Biochemistry*, 20:3615, 1981 and U.S. Pat. No. 4,381,444) were added and the reaction incubated at 37° C. After 20 days the reaction was filtered. Methanol was added to the filtrate to precipitate the protein and the suspension was filtered. The title compound which was contained in the filtrate was purified by successive chromatography on AG1X2-hydroxide (Bio-Rad) with water as the solvent followed by silica gel with acetonitrile/water (95/5) as the solvent followed by silica gel with chloroform/methanol/water (85/15/1.5) as the solvent. Lyophilisation yielded 0.045 g, of the title compound that analysed as a hydrate.

Anal. Calc. for $C_{13}H_{17}FN_6O_3.H_2O$:. Calcd.: C, 45.61; H, 5.59; N, 24.55.

Found: C, 45.80; H, 5.54; N, 24.43.

Structure further confirmed by $^1$H-NMR.

EXAMPLE 4

2-Amino-9-(2-deoxy-2-fluoro-β-D-arabinofuranosyl)-6-methoxy-9H-purine

2-Amino-6-methoxypurine (0.4 g, 2.4 mmoles) which may be prepared according to R. W. Balsiger and J. A. Montgomery *J. Org. Chem.*, 20: 1573, 1960) and 1-(2-deoxy-2-fluoro-β-D-arabinofuranosyl)thymine (C. H. Tann et al., *J. Org. Chem.*, 50:3647, 1985; 0.4 g; 1.5 mmoles) were suspended in 20 ml of 5 mM potassium phosphate buffer, pH 7.0, which contained 0.04% (w/v) potassium azide. The pH of the suspension was adjusted to 7.0 with KOH. Thymidine phosphorlyase (12,000 I.U) and purine nucleoside phosphorylase (16,600 I.U). (T. A. Krenitsky et al., *Biochemistry*, 20:3615, 1981 and U.S. Pat. No. 4,381,444) were added and the suspension stirred at 37° C. On day 3, an additional 8,000 I.U. thymidine phosphorylase and 11,100 I.U. of purine nucleoside phosphorylase were added. On day 15, the reaction was diluted to 200 ml with 5 mM potassium phosphate buffer, pH 7.0, which contained 0.05% (w/v) potassium azide. The pH of the reaction was adjusted to 7.0 with KOH and 8,000 I.U thymidine phosphorylase and 11,100 I.U. purine nucleoside phosphorylase were added. On day 20, the pH of the reaction was adjusted to 7.2 with KOH and 8,000 I.U. thymidine phosphorylase and 11,100 I.U. purine nucleoside phosphorylase were added. On day 43, 0.2 g of 1-(-2-deoxy-2-fluoro-β-D-arabinofuranosyl)thymine was added. The pH of the reaction was adjusted to 6.9 with 10 mM $H_3PO_4$ and 8,000 I.U. thymidine phosphorylase and 2,800 I.U. purine nucleoside phosphorylase added. On day 63, the suspension was filtered. The filtrate was evaporated. The residue was dissolved in water and 2 volumes of methanol added to precipitate the protein. The suspension was filtered and the filtrate evaporated.

The residue was dissolved in water and applied to a 2.5×8 cm AG1X2-hydroxide (Bio-Rad) column. After washing the column with water and methanol/water (1/1), the product was eluted with methanol/water (9/1). Product containing fractions were combined and the solvent removed under vacuum. The residue was dissolved in chloroform/methanol/water (90/10/1) and applied to a 2.5×55 cm silica gel column. The column was eluted with chloroform/methanol/water (90/10/1). Product containing fractions were combined and the solvent removed under vacuum. The residue was dissolved in water and lyophilisation yielded 0.021 g of title compound that analysed as a 0.5 hydrate.

Anal. Calcd. for $C_{11}H_{14}FN_5O_4 0.5\ H_2O$.

Calcd.: C, 42.86; H, 4.90; N, 22.72. Found: C, 42.92; H, 4.93; N, 22.61.

Structure further confirmed by $^1$H-NMR.

EXAMPLE 5

2-Amino-9-(2-deoxy-2-fluoro-β-D-arabinofuranosyl)-6-ethoxy-9H-purine

2-Amino-6-ethoxypurine (0.5 g, 2.8 mmoles) which may be prepared according to R. W. Balsiger and J. A. Montgomery *J. Org. Chem.*, 25:1573, 1960) and 1-(2-deoxy-2-fluoro-β-D-arabinofuranosyl)thymine (C. H. Tann et al., *J. Org. Chem.*, 50:3647, 1985; 0.5 g; 1.9 mmoles) were suspended in 25 ml of 5 mM potassium phosphate buffer, pH 7.0, which contained 0.04% (w/v) potassium azide. Thymidine phosphorylase (8,000 I.U) and purine nucleoside phosphorylase (11,100 I.U.) (T. A. Krenitsky, et al., *Biochemistry*, 20:3615, 1981 and U.S. Pat. No. 4,381,444) were added and the reaction stirred at 37° C. On day 24, 8,000 I.U. of thymidine phosphorylase and 5,500 I.U. of purine nucleoside phosphorylase were added. On day 49, the reaction was diluted to 250 ml with 5 mM potassium phosphate buffer, pH 7.0, which contained 0.04% (w/v) potassium azide. The pH of the reaction was adjusted to 7.0 with KOH and 12,000 I.U. of thymidine phosphorylase and 8,300 I.U. of purine nucleoside phosphorylase were added. On day 79, the solvent was removed under vacuum. The residue was dissolved in hot water and two volumes of acetonitrile added to precipitate the protein. After standing overnight the suspension was filtered. The filtrate was evaporated. The residue was dissolved in hot water and then allowed to cool to 25° C. The suspension was filtered and the filtrate applied to a 2.5×8 cm AG1X2-hydroxide (Bio-Rad) column. After washing the column with water and methanol/water (1/1) the product was eluted with methanol water (9/1). Product containing fractions were combined and the solvent removed under vacuum. The residue was dissolved in chloroform/methanol/water (90/10/1) and applied to a 2.5×55 cm silica gel column. The column was eluted with chloroform/methanol/water (90/10/1). Product containing fractions were combined and the solvent removed under vacuum. The residue was dissolved in water and lyophilisation yielded 0.041 g of title compound that analysed as 0.4 hydrate.

Anal. Calcd. for $C_{12}H_{16}FN_5O_4 \cdot 0.4\ H_2O$.

Calcd.: C, 44.97; H, 5.28; N, 21.85. Found: C, 44.97; H, 5.33; N, 21.85.

Structure further confirmed by $^1$H-NMR.

EXAMPLE 6

2-Amino-9-(2-deoxy-2-fluoro-$\beta$-D-arabinofuranosyl)-9H-purine

2-Aminopurine (Pacific Chemical Laboratories, 0.3 g, 2.2 mmoles) and 1-(2-deoxy-2-fluoro-$\beta$-D-arabinofuranosyl)thymine (C. H. Tann et al., *J. Org. Chem.*, 50:3647, 1985; 0.3 g; 1.2 mmoles) were suspended in 25 ml of 5 mM potassium phosphate buffer, pH 7.0, which contained 0.04% (w/v) potassium azide. Thymidine phosphorylase (12,000 I.U.) (T. A. Krenitsky, et. al, *Biochemistry*, 20:3615, 1981) was added and the suspension stirred at 37° C. On day 3, 5,500 I,U, of purine nucleoside phosphorylase (T. A. Krenitsky, et al., *Biochemistry*, 20:3615, 1981 and U.S. Pat. No. 4,381,444) was added. On day 18, the reaction was diluted to 200 ml with 5 mM potassium phosphate buffer, pH 7.0, which contained 0.4% (w/v) potassium azide. On day 26, 0.4 g of 2-aminopurine, 8,000 I.U. of thymidine phosphorylase, and 2,800 I.U. of purine phosphorylase were added. On day 41, 0.2 g of 1-(2-deoxy-2-fluoro-$\beta$-D-arabinofuranosyl)thymidine, 8,000 I.U. of thymidine phosphorylase and 2,800 I.U. of purine nucleoside phosphorylase were added. On day 48, the reaction was diluted to 1,000 ml with 5 mM potassium phosphate buffer, pH 7.0 which contained 0.04% (w/v) potassium azide and 2.0 g of 2-aminopurine, 16,000 I.U. of thymidine phosphorylase and 5,500 I.U. purine nucleoside phosphorylase were added. On day 54, 1 g of 2-aminopurine, 8,000 I.U. of thymidine phosporylase, and 2,800 I.U. of purine nucleoside phosphorylase were added. On day 68, the suspension was evaporated to near dryness. Three volumes of ethanol were added to precipitate the protein and the suspension filtered. The title compound which was contained in the filtrate was purified by chromatography on AG1X2-hydroxide (Bio-Rad) with methanol/water (9/1) as the solvent followed by chromatography on silica gel with acetonitrile/water (95/5) as the solvent. Lyophilisation yielded 0.13 g of the title compound that analysed as a 0.3 hydrate.

Anal. Calcd. for $C_{10}H_{12}FN_5O_3 \cdot 0.3\ H_2O$.

Calcd.: C, 43.73; H, 4.62; N, 25.50; F, 6.92. Found: C, 43,47; H, 4.65; N, 25.22; F, 7.17.

Structure further confirmed by $^1$H-NMR.

EXAMPLE 7

Tablet Formulations

The following formulations A, B and C are prepared by wet granulation of the ingredients with a solution of povidone, followed by addition of magnesium stearate and compression. the reaction was diluted to 1,000 ml with 5 mM potassium phosphate buffer, pH 7.0 which contained 0.04% (w/v) potassium azide and 2.0 g of 2-aminopurine, 16,000 I.U. of thymidine phosphorylase and 5,500 I.U. purine nucleoside phosphorylase were added. On day 54, 1 g of 2-aminopurine, 8,000 I.U. of thymidine phosporylase, and 2,800 I.U. of purine nucleoside phosphorylase were added. On day 68, the suspension was evaporated to near dryness. Three volumes of ethanol were added to precipitate the protein and the suspension filtered. The title compound which was contained in the filtrate was purified by chromatography on AG1X2-hydroxide (Bio-Rad) with methanol/water (9/1) as the solvent followed by chromatography on silica gel with acetonitrile/water (95/5) as the solvent. Lyophilisation yielded 0.13 g of the title compound that analysed as a 0.3 hydrate.

Anal. Calcd. for $C_{10}H_{12}FN_5O_3 \cdot 0.3\ H_2O$.

Calcd.: C, 43.73; H, 4.62; N, 25.50; F, 6.92. Found: C, 43.47; H, 4.65; N, 25.22; F, 7.17.

Structure further confirmed by $^1$H-NMR.

EXAMPLE 7

Tablet Formulations

The following formulations A, B and C are prepared by wet granulation of the ingredients with a solution of povidone, followed by addition of magnesium stearate and compression.

|  | mg/tablet | mg/tablet |
|---|---|---|
| Formulation A | | |
| (a) Active ingredient | 250 | 150 |
| (b) Lactose B.P. | 210 | 126 |
| (c) Povidone B.P. | 15 | 9 |
| (d) Sodium Starch Glycollate | 20 | 12 |
| (e) Magnesium Stearate | 5 | 3 |
|  | 500 | 300 |
| Formulation B | | |
| (a) Active ingredient | 250 | 150 |
| (b) Lactose | 150 | 90 |
| (c) Avicel PH 101 | 60 | 36 |
| (d) Povidone B.P. | 15 | 9 |
| (e) Sodium Starch Glycollate | 20 | 12 |
| (f) Magnesium Stearate | 5 | 3 |
|  | 500 | 300 |
| Formulation C | | |
| Active ingredient | 100 | |
| Lactose | 200 | |
| Starch | 50 | |
| Povidone | 5 | |
| Magnesium stearate | 4 | |
|  | 359 | |

The following formulations, D and E, are prepared by direct compression of the admixed ingredients. The lactose in formulation E is of the direct compression type.

|  | mg/tablet |
| --- | --- |
| Formulation D | |
| Active ingredient | 250 |
| Pregelatinised Starch NF15 | 148 |
| Magnesium Stearate | 2 |
| | 400 |
| Formulation E | |
| Active ingredient | 250 |
| Lactose | 150 |
| Avicel | 98 |
| Magnesium Stearate | 2 |
| | 500 |

Formulation F (Controlled Release Formulation)

The formulation is prepared by wet granulation of the ingredients (below) with a solution of povidone followed by the addition of magnesium stearate and compression.

|  | mg/tablet |
| --- | --- |
| (a) Active ingredient | 500 |
| (b) Hydroxypropylmethylcellulose (Methocel K4M Premium) | 112 |
| (c) Lactose B.P. | 53 |
| (d) Povidone B.P | 28 |
| (e) Magnesium Stearate | 7 |
| | 700 |

Drug release takes place over a period of about 6–8 hours and is complete after 12 hours.

EXAMPLE 8

Capsule Formulations

Formulation A

A capsule formulation is prepared by admixing the ingredients of Formulation D in Example 1 above and filling into a two-part hard gelatin capsule. Formulation B (infra) is prepared in a similar manner.

|  | mg/capsule |
| --- | --- |
| Formulation B | |
| (a) Active ingredient | 250 |
| (b) Lactose B.P. | 143 |
| (c) Sodium Starch Glycollate | 25 |
| (d) Magnesium Stearate | 2 |
| | 420 |
| Formulation C | |
| (a) Active ingredient | 250 |
| (b) Macrogol 4000 B.P. | 350 |
| | 600 |

Capsules of formulation C are prepared by melting the Macrogol 4000 BP, dispersing the active ingredient in the melt and filling the melt into a two-part hard gelatin capsule.

|  | mg/capsule |
| --- | --- |
| Formulation D | |
| Active ingredient | 250 |
| Lecithin | 100 |
| Arachis Oil | 100 |
| | 450 |

Capsules of formulation D are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients a, b and c using an extruder, followed by spheronisation of the extrudate and drying. The dried pellets are then coated with release-controlling membrane (d) and filled into a two-piece, hard gelatin capsule.

|  | mg/capsule |
| --- | --- |
| (a) Active ingredient | 250 |
| (b) Microcrystalline Cellulose | 125 |
| (c) Lactose B.P. | 125 |
| (d) Ethyl Cellulose | 13 |
| | 513 |

EXAMPLE 9

Injectable Formulation

| Active ingredient | 0.200 g |
| --- | --- |
| Hydrochloric acid solution, 0.1 M q.s. to | pH 4.0 to 7.0 |
| Sodium hydroxide solution, 0.1 M q.s. to | pH 4.0 to 7.0 |
| Sterile water q.s. to | 10 ml |

The active ingredient is dissolved in most of the water (35°–40° C.) and the pH adjusted to between 4.0 and 7.0 with the hydrochloric acid or the sodium hydroxide as appropriate. The batch is then made up to volume with the water and filtered through a sterile micropore filter into a sterile 10 ml amber glass vial (type 1) and sealed with sterile closures and overseals.

| Formulation B | |
| --- | --- |
| Active ingredient | 0.125 g |
| Sterile pyrogen-free, pH 7 phosphate buffer, q.s. to | 25 ml |

EXAMPLE 10

Intramuscular Injection

|  | Weight (g) |
| --- | --- |
| Active ingredient | 0.20 g |
| Benzyl Alcohol | 0.10 g |
| Glycofurol 75 | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml amber glass vials (type 1).

Example 11:

Syrup

|  | Weight (g) |
| --- | --- |
| Active ingredient | 0.25 g |
| Sorbitol Solution | 1.50 g |
| Glycerol | 2.00 g |
| Sodium Benzoate | 0.005 g |
| Flavour, Peach 17.42.3169 | 0.0125 ml |
| Purified Water q.s. to | 5.00 ml |

The active ingredient is dissolved in a mixture of the glycerol and most of the purified water. An aqueous solution of the sodium benzoate is then added to the solution, followed by addition of the sorbitol solution and finally the flavour. The volume is made up with purified water and mixed well.

When the active ingredient is poorly soluble, the following formulation (B) is used.

|  | Weight (g) |
| --- | --- |
| Formulation B | |
| Active ingredient | 0.25 g |
| Sorbitol Solution | 1.50 g |
| Glycerol | 0.75 g |
| Dispersible Cellulose | 0.1 g |
| Sodium Benzoate | 0.005 g |
| Flavour | q.s. |
| Purified Water to | 5.000 ml |

The sorbitol solution is mixed with the glycerol and part of the purified water. The sodium benzoate in dissolved in purified water and added to the bulk. The dispersible cellulose and flavour is added and dispersed. The active ingredient is then added and dispersed and volume is made up with purified water.

EXAMPLE 12

Suppository

|  | mg/suppository |
| --- | --- |
| Active ingredient (63 μm)* | 250 |
| Hard Fat, BP (Witpesol H15 - Dynamit NoBel) | 1770 |
|  | 2020 |

*The active ingredient is used as a powder wherein at least 90% of the particles are of 63 μm diameter or less.

One-fifth of the Witepsol H15 is melted in a steam-jacketed pan at 45° C. maximum. The active ingredient is sifted through a 200 μm sieve and added to the molten base with mixing, using a silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 40° C. At a temperature of 38° C. to 40° C., 2.02 g of the mixture is filled into suitable, 2 ml plastic moulds. The suppositories are allowed to cool to room temperature.

EXAMPLE 13

Pessaries

|  | mg/pessary |
| --- | --- |
| Active ingredient (63 μm) | 250 |
| Anhydrous Dextrose | 380 |
| Potato Starch | 363 |
| Magnesium Stearate | 7 |
|  | 1000 |

The above ingredients are mixed directly and pessaries prepared by direct compression of the resulting mixture.

Antiviral Activity 9-(2-deoxy-2-fluoro-β-D-arabinofuranosyl) guanine was tested for activity against HIV in vitro in accordance with the method described by H. Mitsuya et al, Proc. Natl. Acad. Sci., USA, Vol 82, pp 7096-7100, October 1985, and found to have activity at a concentration of 1 μM.

Toxicity

Cell toxicity is assessed in a cell growth inhibition assay. Subconfluent cultures of Vero cells grown on 96-well microtiter dishes are exposed to different dilutions of drug, and cell viability determined daily on replicate cultures using uptake of a tetrazolium dye (MTT). The concentration required for a 50% inhibition of cell viability at 96 hours is termed $CCID_{50}$. The $CCID_{50}$ for 9-(2-deoxy-2-fluoro-β-D-arabinofuranosyl) guanine was 39 μM.

We claim:

1. 2-amino-6-(cyclopropylamino)-9-(2-deoxy-2-fluoro-β-D-arabinofuranosyl)-9H-purine.

* * * * *